United States Patent [19]

Richards

[11] Patent Number: 4,921,349

[45] Date of Patent: May 1, 1990

[54] PHOTOGRAPHIC METHOD FOR MONITORING VISIBILITY THROUGH MEASUREMENT OF TRANSMITTANCE AND PATH RADIANCE

[75] Inventor: L. Willard Richards, Santa Rosa, Calif.

[73] Assignee: Sonoma Technology, Santa Rosa, Calif.

[21] Appl. No.: 68,265

[22] Filed: Jun. 30, 1987

[51] Int. Cl.$^5$ ............................................. G01N 21/49
[52] U.S. Cl. ..................................... 356/229; 356/438
[58] Field of Search ............... 356/437, 438, 439, 229, 356/437, 438, 439, 230

[56] References Cited

U.S. PATENT DOCUMENTS

| 2,198,971 | 4/1940 | Neufeld | 356/437 |
| 3,672,781 | 6/1972 | Rosenblum | 356/438 |
| 3,841,763 | 10/1974 | Lewis | 356/438 |

OTHER PUBLICATIONS

Malm, W. C. *J. Air Poll. Contr. Assoc.* 1979, 29, 1042–1052.
Malm, W. C.; Walther, E. G.; O'Dell, K.; Kleine, M. *Atmos. Environ.* 1981, 15, 2031–2042.
Tombach, I. H.; Allard, D. W.; Drake, R. L.; Lewis, R. C. "Western Regional Air Quality Studies, Visibility and air Quality Measurements: 1981-1982"; AeroVironment Interim Report Electric Power Research Inst., Research Project 1630-11, Jan. 1987.
White, W. H.; Macias, E. S.; "Uncertainties in the Atmospheric Extinction Inferred From Teleradiometry of Natural Targets"; presented at APCA International Specialty Conf., Visibility Protection–Research & Policy Aspects. Grand Teton Nat'l park, Wy., 7–10 Sep. 1986.
Richards, L. W.; "Optical Measurements for Visibility Monitoring and Research"; submitted to *J. Air. Poll. Contro. Assoc.*, 1987.
Malm, W. C.; Persha, G.; Tree, R.; Stocker, R.; Tombach, I.; Iyer, H. "Comparison of Atmospheric Extinction Measurements Made By a Transmissometer, Integrating Nephelometer, & Teleradiometer with Natural & Artificial Black Target"; presented at APCA Int'l Specialty Conf. Visibility Protec.–Research & Policy Aspects. Grand Teton Nat'l Park, Wy., 7–10 Sep. 1986.
Middleton, W. E. K. *Vision Through the Atmosphere;* University of Toronto Press: Toronto, 1958. See Section 6.6.
Steffens, C. *Ind. & Eng. Chem.* 1949, 41, 2396–2399.
Roberts, E. M.; Gordon, J. L.; "Documentation of Visibility in the Painted Desert Petrified Forest National Park for Arizona Public Service"; Dames and Moore Report No. 2353-010-02, Jun. 1974.
Johnson, C. E.; Malm, W. C.; Persha, G.; Molenar, J. V.; Hein, J. R. *J. Air. Poll. Contr. Assoc.* 1985, 35, 1261–1265.
Haecker, G. *Meteorol. Zeit.* 1905, 22, 343–353.
Duntley, S. O. *J. Opt. Soc. Am.* 1948, 38, 179–191.
Duntley, S. O.; Boileau, A. R.; Preisendorfer, R. W. *J. Opt. Soc. Am.* 1957, 47, 499–506.
White, W. H. *Atmos. Environ.* 1986, 20, 1659–1672.
Sloane, C. S. *Atmos Environ.* 1986, 20, 1025–1037.
Richards, W. L.; Steolting, M. "Experimental Evaluation of the Determination of Atmospheric Extinction by the Measurement of the Transmittance of Radiance Differences"; presented at APCA Int'l Speciality Conf., Visibility Protection–Research and Policy Aspects. Grand Teton National Park, Wy., 7–10 Sep. 1986.

Primary Examiner—Richard A. Rosenberger
Attorney, Agent, or Firm—Limbach, Limbach & Sutton

[57] ABSTRACT

A photographic method of collecting and reducing photographic film density data for monitoring air quality is disclosed in which photographic film is first calibrated using calibration scales of known reflectance and the measured radiance of one calibration scale step to relate the photographic film density to the known radiance. Measurement of a target's radiance and sight path radiance is made via target photographic image density analysis and mathematical expressions which convert density information into radiance and/or atmospheric transmittance data using expressions developed from the calibration scale data.

13 Claims, 4 Drawing Sheets

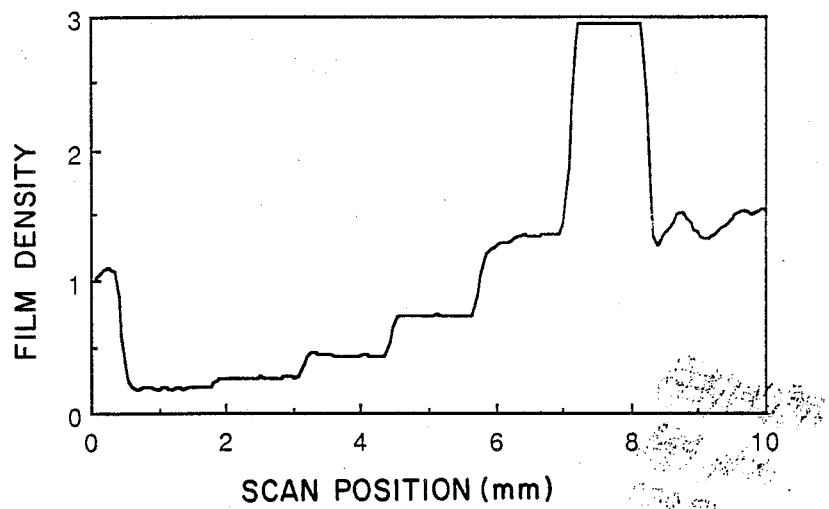
FILM DENSITY SCAN FOR
A CALIBRATION GRAY SCALE
FIG_2
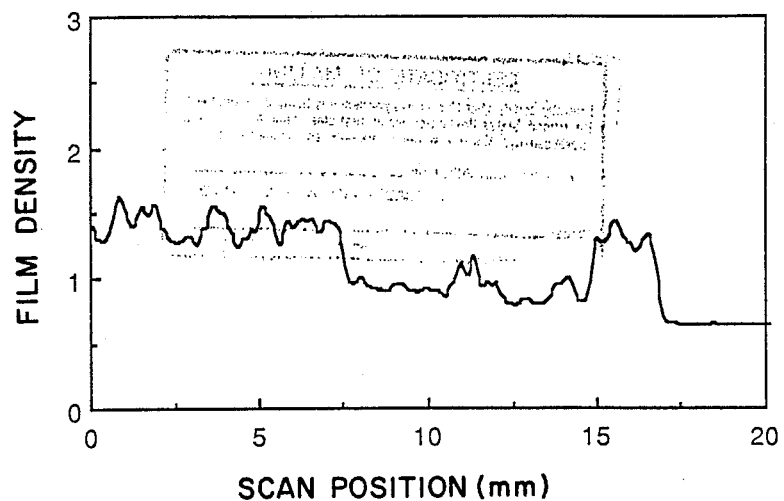
FILM DENSITY SCAN FOR
A SCENE
FIG_3

PHOTOGRAPHIC METHOD FOR MONITORING VISIBILITY THROUGH MEASUREMENT OF TRANSMITTANCE AND PATH RADIANCE

TECHNICAL FIELD OF THE INVENTION

The present invention relates generally to air quality instrumentation, data collection and visibility monitoring, and more specifically to the use of photographic data collecting and reducing techniques to obtain quantitative atmospheric transmittance and path radiance data sufficient to characterize visibility.

BACKGROUND OF THE INVENTION

Haze and reduced visibility are the effects of air pollution most noticed by the general public, and are often thought of by the public as a measure of air quality. The adverse effects of air pollution on the clarity of the air are especially undesirable in remote wilderness areas and in the National Parks, where the scenic vistas are an important part of the visitor's experience. The U.S. Congress has sought in the 1977 Amendments to the Clean Air Act to preserve visibility, and set as a national goal "the prevention of any future and remedying of any existing impairment of visibility in any mandatory Class I Federal area which impairment results from manmade air pollution." Class I Federal areas include most of the national parks, larger wildernesses, and international parks. To obtain the technical data necessary to learn about the origins of visibility reducing hazes and to monitor progress towards achieving this goal, it is necessary to measure the optical properties of our atmosphere which relate to visibility. It is desirable to have a simple, reliable, cost effective method for monitoring visibility, which is practical for use even in remote areas.

Visibility monitoring is performed by government agencies to obtain data to protect the public interests. Monitoring must also be performed by industrial operations to understand the effects of their emissions and to obtain data which may be submitted in support of permit applications.

In recent years, most visibility monitoring in remote areas has been done by the measurement of the contrast of distant terrain features against the horizon sky (Malm, 1979; Malm et al., 1981; Tombach et al., 1987). An analysis of pairs of measurements taken close to each other has shown that this measurement method gives results which show considerable scatter, even when the sky is relatively free of clouds (White and Macias, 1986). This outcome can easily be explained by the variable illumination of the target and the sight path caused by many factors, including the variations in the reflectance of the ground (Richards, 1987). Because of the significant uncertainties in transmittances calculated from contrast measurements, there is a need for a better monitoring method.

In an attempt to fill this need, the National Park Service has sponsored the development of a transmissometer. The resulting instrument (Malm et al., 1986) is expensive, and does not provide data for the path radiance, which is shown below to be an important omission.

Photographic methods have long been used for visibility monitoring (Middleton, 1958; Steffens, 1949; Roberts and Gordon, 1974; Johnson et al., 1985). They have the advantage that photographic equipment is inexpensive to purchase and to operate unattended. Photographic visibility monitoring methods in current use typically attempt to measure the contrast of distant terrain features against the horizon sky. The demonstration by White and Macias (1986) of the unreliability of visibility data derived from instrumental measurements of contrast, which are of higher quality than can be obtained from photographs, shows that the contrast measurements derived from photographic data must also be unreliable.

This invention fulfills the need for a simple, reliable visibility monitoring method which uses equipment of reasonable cost and which can be easily used in remote locations. It is an important feature of the invention that both the transmittance and path radiance of sight paths are measured.

SUMMARY OF THE INVENTION

A method for obtaining quantitative data useful to determine either the transmittance, path radiance, or both, of a sight path between at least two camera stations toward a target having both relatively light and dark areas using photographic film comprises the steps of (a) at each of at least two stations along a sight path, providing a camera with photographic film, a calibration scale having panels of known reflectance in the camera's field of view, a light meter, and means for synchronizing the time of the photographic exposures; (b) at each station along the sight path, photographing a target having varying light contrast substantially synchronously with all other stations; (c) calibrating the photographic film at each station by recording the light meter reading for the radiance of at least one of the calibration panels at each station at the time of the target exposure; and, (d) obtaining radiance data for each station along the sight path by using the step (c) radiance calibration obtained by measuring the photographic film densities corresponding to the calibration scale panels and by measuring the film densities for each target photograph for contrasting portions of the target. A method for reducing the data so obtained is disclosed wherein the known reflectances of the calibration scale steps and the radiance of one of the steps measured at the time the photograph was taken is used to calculate the radiance of all the calibration scale steps. A graph or mathematical expression is then derived relating the radiance of each recorded calibration scale step to the density of its image recorded on the photographic film. This graph or mathematical expression is then used to convert measured film densities into apparent radiances for a series of points in the target scene in the photographs taken at each of the stations on the sight path. Equation (1) $I = I_o T + I_p$ for two or more points in the target is then used to calculate either transmittance, path radiance, or both, between camera stations.

BRIEF DESCRIPTION OF THE FIGURES

FIG. 2 is a photographic film density scan for a gray scale used for calibration according to the instant invention.

FIG. 3 is a film density scan for a target scene.

DETAILED DESCRIPTION OF THE INVENTION

Figure 1:
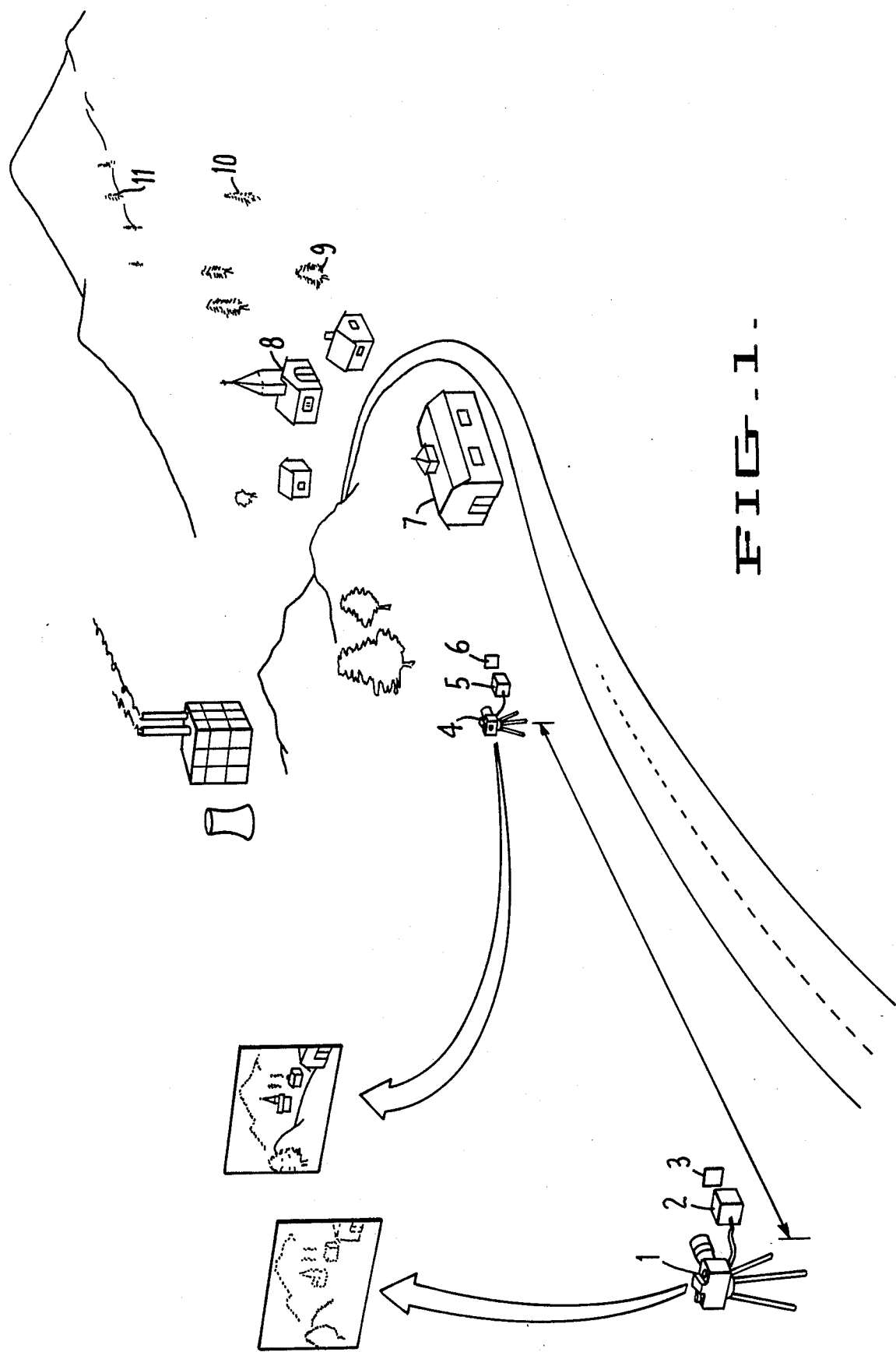
FIG. 1 is a schematic diagram of field installed monitoring apparatus according to the present invention.

It is useful to provide a brief review of the optical properties of approximately horizontal sight paths through the atmosphere in order to more fully develop the background of this invention. Some of this theory has been described by previous authors, the relevant portions of which are hereby incorporated by reference (Duntley, 1948; Duntley et al., 1957; Malm, 1979).

It is recommended to make measurements of the optical properties of the atmosphere with radiation in a restricted wavelength range. Some optical properties of the atmosphere, especially light scattering by very small particles and air molecules, depend strongly on wavelength, so measurements made with broad ranges of wavelengths are not easily interpreted. The human eye is most sensitive in the green, so when measurements are made only in one wavelength range, it is preferred to make these measurements with green light, and this is standard practice.

When an observer gazes on a scene, light from the viewed target travels through the atmosphere to the eye. The straight line from a target being viewed to the observer's eye is a sight path. The radiance of a ray of light on this sight path is equal to the rate of energy transfer through an area perpendicular to the ray divided by the product of the area, the solid angle of view, and the wavelength range.

The initial radiance $I_o$ is the radiance measured at some point which can be considered the initial point on the sight path. The apparent radiance is the radiance entering the eye or measurement instrument a distance x from the point where initial radiance is measured. The transmittance of the sight path is equal to the fraction of the initial radiance which traverses the sight path and reaches the location where the apparent radiance is measured. Therefore, the transmitted radiance is $I_oT$.

Some of the apparent radiance is due to light which is first scattered into the sight path by the atmosphere in the sight path and then transmitted to the measurement instrument or the observer's eye. This light, which is caused by the illumination of the atmosphere in the sight path, is the path radiance $I_p$.

The apparent radiance is always equal to the sum of the transmitted radiance $I_oT$ and the path radiance $I_p$:

$$I = I_o T + I_p. \tag{1}$$

Thus, light entering the eye from a sight path to a distant object comes from two sources: one source is the object itself, which contributes the transmitted radiance, and the other is the intervening atmosphere, which contributes the path radiance.

The transmittance and path radiance of a sight path are necessary and sufficient to characterize the visibility along the sight path. Therefore, the ability to measure these quantities is of great practical interest. It can be shown that the transmittance and path radiance are sufficient to characterize visibility by noting that they can be used in Equation 1 to calculate the apparent radiance corresponding to any initial radiance. Very intense laser beams which physically modify the atmosphere in the sight path by heating the air are an exception. Such calculations are valid for the sight path, times, and wavelengths of the monitoring data.

Parameters related to human vision, such as contrast and modulation, are calculated from apparent radiances. Thus, a knowledge of the transmittance and path radiance of a sight path make it possible to calculate how the atmosphere in the sight path transforms initial radiances into apparent radiances, and hence how the atmosphere in the sight path affects parameters related to human vision.

The necessity of measuring both transmittance and path radiance can be established by showing it is not possible to derive one parameter from the other. This is obvious when day to night variations are considered. When the illumination of the sight path becomes very small at night, the path radiance becomes very small. It is also true that the path radiance need not correlate with the transmittance even when the illumination of the sight path is constant. Absorption has opposite effects on transmittance and path radiance. Adding absorption to the atmosphere changes the transmittance in a direction which degrades visibility while the path radiance is changed in a direction which improves visibility.

The transmittance of a sight path has the very useful property that light extinction is independent of the illumination and is closely linked to air quality by relationships that are well understood but difficult to apply in practice (White, 1986; Sloane, 1986). Because of the close relationship to air quality and its effect on apparent radiances, it is highly desirable that visibility monitoring programs monitor the transmittance of sight paths.

It is important to measure the path radiance because of its large effect on apparent radiances. For example, when the atmosphere is very clear and the visual range is 200 km, the path radiance will contribute more to the apparent radiance than will the transmitted radiance for a sight path to a wooded hillside only 9 km away. In this example, it was assumed that the initial radiance of the wooded hillside was 20% of the radiance of the horizon sky. It is a good generalization that when a scene is far enough away that visibility is of concern, most of the apparent radiance is due to the path radiance.

The present invention provides a method for obtaining quantitative data for the transmittance, or path radiance, or both, of a sight path from photographic film, such as color transparencies. To do this, it is necessary to calibrate the film so that radiances can be calculated from measured film densities. This is accomplished by including in the photograph a gray scale with panels of known reflectance and recording the radiance of one of the panels. It is also necessary to take photographs of the same target scene at the same time (substantially synchronously) at two distances along a sight path. The transmittance and path radiance determined from the photographs is for the sight path between the locations of the two cameras. The radiances from the two photographs can be on any arbitrary scale of radiance, but the same radiance scale must be used for each photograph in a pair. The values for the path radiance obtained from the photographs will be on this scale, so it is desirable to obtain an absolute calibration of the radiances.

While the instant invention is described with reference to a particularly preferred embodiment, it will be apparent to those of ordinary skill in the art that calibration scales other than gray scales may be used to practice the instant invention. The use of other graduated density panels to calibrate the photographic film is intended to be within the scope of the claims appended hereto.

The data recorded on the photographs are reduced by first measuring the photographic film densities for the gray scale steps to calibrate the film and then measuring the film densities along a line through a portion of the target scene containing relatively light and dark areas. The film calibration data are used to convert the measured photographic film densities for the scan of the target scene into radiance values. The scans of the same target scene taken at the same time are expanded and shifted as necessary to bring the target images into register. The radiances from the near photograph are $I_o$ in Equation 1, and from the far photograph are I. A regression analysis can be performed on these values of I and $I_o$ to determine the best fit values of the transmittance and path radiance.

In the preferred embodiment, except for the lens focal lengths, the apparatus required for these measurements is the same at each location: an automatic exposure camera, a gray scale in the field of view of the camera, a light meter to make the radiance reading of one step of the calibration (gray) scale at the time of the photograph available for recording, and means for controlling and synchronizing the times of the photographs. The latter two functions can be provided by a light meter-timer. The lens focal lengths should be inversely proportional to the distance of the camera from the target, so that the images of the target are nearly the same size in each photograph. The light meter-timer system triggers the cameras at each station along the sight path substantially synchronously, to read and make available for recording the radiance of one panel of the gray scale at the time of each photograph. The equipment may be housed in a shelter to protect it from the elements.

A schematic diagram of a suitable arrangement of the measurement equipment is shown in FIG. 1. A camera 1 at a distance from the target scene is focused on scenic elements 7–11. A gray scale 3 is in the field of view of the camera, and a light meter-timer system 2 controls the times when the photographs are taken and provides radiance data to be recorded in the photograph. In some embodiments, a display controlled by the light meter-timer system 2 is in the field of view of the camera. The gray scale need not be far enough from the camera to be in sharp focus, but it should be nearly enough in focus that the circle of confusion due to the lack of focus should have a diameter less than roughly ¼ the width of the image of one panel of the gray scale.

A camera 4 closer to the target scene is also focused on scenic elements 7–11, has a gray scale 6 in the field of view, and has a light meter-timer system 5, which in some embodiments controls a display in the field of view. Scenic elements 7–11 may be at various distances from the cameras, but it is preferable that they not be so widely separated that some of them are out of focus. The sight path from camera 1 to the scenic elements must pass close to camera 4 so that the radiances recorded by camera 4 are a good measure of the initial radiances $I_o$ on the sight path between the two camera locations.

A great variety of scenic elements 7–11 are suitable. The most important requirement is that the scene include both light and dark areas which are large enough to be resolved both in the photographs and by the densitometer which scans the photographs. In settled areas, buildings 7, 8, trees 9, 11, and unforested ground or rocks 10 can give adequate contrast. In remote areas, forested areas, rocks or cliffs, snow patches, etc. can be used. When the scene is scanned by the densitometer, it is preferable to avoid using portions of the scene with fine detail which cannot be resolved by the densitometer. When possible, it is recommended that the camera lens focal lengths be inversely related to the distance between the camera and the target scene so that the scenic element images will be approximately the same size in each photograph. When this is the case, any limitations caused by the resolution of the film or by the densitometer will have nearly the same effect on all density scans and will tend to cancel out in the data reduction.

It is specifically contemplated that various targetscenes may be used, so long as these targets have varying light contrast. Natural scenic elements maybe used as the target. Man-made elements such as buildings may be used as the target elements. Combinations of natural scenic and man-made elements are possible. It is also possible that a specific target apparatus can be constructed.

Because some optical properties of the atmosphere, such as the light scattering by air molecules, have a strong dependence on wavelength, it is recommended that the photographic images be produced by light of limited wavelength range. When using black-and-white film, the wavelength of light can be limited to a narrow range by a color filter. Positive color transparency film contains three dye layers, each of which responds to light of limited wavelength range. Thus, the use of color slide film allows simultaneous measurements for each of three wavelengths ranges and also produces a photographic record of the appearance of the scene at the time the data were recorded.

The light meter-timer systems 2 and 5 have two functions. One is triggering the cameras at times when visibility measurements are desired. Because cloud shadows can cause rapid changes in the radiances of the target scenic elements, it is necessary that the two photographic exposures be closely synchronized in time. Synchronization to a within one second is preferred, but timing errors of a few seconds can be tolerated. The other function of the light meter-timer systems is to measure the radiance of one panel of the film calibration gray scale and to display this value making the information available for recording in the photograph.

When black-and-white film is used, it is recommended that the same type of color filter be used on the light meter and the camera. When color transparency film is used, it is recommended that the light meter respond to green light within a range of wavelengths corresponding to the maximum response of the magenta-forming layer in the film, which is the layer that responds to green light. An interference filter with a maximum transmittance at 550 nm has been used on the light meter, but gelatin and glass filters with satisfactory characteristics are available.

Gray scales which are diffuse reflectors, i.e., which have a non-glossy surface and reflectance values of 1.4, 9.0, 19.8, 36.2, 59.1, and 90 percent reflectance have been used. Glossy surfaces were avoided because of the potential for distortions caused by reflected images. Gray scales with more steps are available and can be used to obtain more complete film calibration data than in the following examples. When the gray scale is placed in uniform illumination, it is necessary to measure the radiance of only one step, and the radiances of the other steps can be calculated from the ratio of the reflectances. In principle, any gray scale step could be used as the reference step whose radiance is measured. Experiments have been performed in which either the 19.8 or the 36.2 percent reflectance steps were used.

Experiments have been performed in which the light meter had a liquid crystal display and was in the field of view of the camera. A lens between the display and the camera created a magnified image of the display at a distance within the depth of focus of the camera. The light meter reading was read from the photograph. Other types of digital displays are commonly available, and any light meter display in the field of view of the camera which can be read in the photograph can be used. It is helpful, but not necessary, to include a clock showing the time and date in the field of view of the camera so this information can also be read from the photographic image.

Data backs which allow recording data directly on the film are available, and have advantages for recording the light meter reading, and optionally, the time and date on the film. This arrangement allows placing the light meter-timer in the same enclosure with the camera, and provides a data recording method which has no dependence on ambient lighting. Other means of recording the light meter readings and times on the film or on the auxiliary data recording devices can be envisaged, and are intended to fall within the scope of this invention and the claims appended hereto.

It is a significant feature of the invention that photographic film calibration data are recorded on each frame. This allows the use of automatic cameras to obtain the optimum exposure for each image and eliminates the need to keep a record of the exposure settings. It also eliminates the need for special handling during film development; any reliable local processing service can be used. Furthermore, if a roll of film is subjected to adverse conditions, such as extreme heat, which might modify the latent images after some but not all of the frames are exposed, the calibration data for each frame will be altered in the same way as the image so that any distortion of the images can be accounted for and corrected during data processing. Recording all data on the photograph itself minimizes the need to record data in a notebook or other auxiliary records.

The data are read from the photographic film by using a densitometer to read the film density along two or more lines in the image. One line extends the length of the gray scale and gives film densities corresponding to each of the steps in the gray scale. One or more other lines extend through the portion(s) of the scene from which it is desired to extract data. It is important that the desitometer scans of the near and far photographs taken at the same time pass through the same portions of the scene. If a scanning densitometer is not available, it is adequate to read the film densities for spots in the images of the steps of the calibration scale and in light and dark parts of the scene.

When color slide film is used, the wavelengths used by the densitometer should provide good color separation. For example, a wavelength of 550 nm gives a good measure of the density of the magenta-forming layer with a minimum of interference from the cyan- and yellow-forming layers. Data for the dye spectra and wavelength sensitivity of each dye layer are available from the film manufacturers and can be used to determine the optimum wavelengths to use for the film density measurements.

Figure 4:
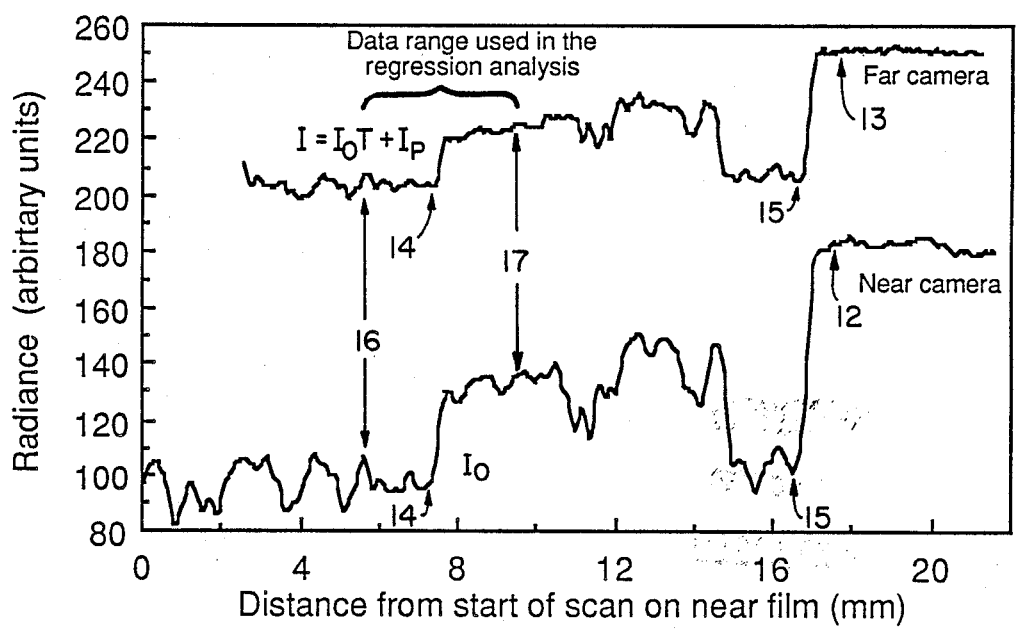
FIG. 4 is a plot of radiance versus distance in the image, known as a radiance profile.

FIG. 2 shows a film density scan measured using a wavelength of 550 nm for an image of a gray scale recorded on Kodachrome 64 slide film. FIG. 3 shows a film density scan for a portion of a scene on the same image. The steps for converting the density scan in FIG. 3 into the radiance profile in FIG. 4 are:

1. Use the known reflectances of the gray scale steps and the radiance of one of the steps measured at the time the photograph was taken and recorded in the photograph to calculate the radiances of all the gray scale steps.
2. Use a regression analysis or similar procedure to derive a mathematical expression relating the radiance of each gray scale step to the density of its image on film.
3. Use this mathematical expression to convert the measured film density at each point on the scan of the target scene into the apparent radiance of this point in the scene.

Various mathematical procedures can be used to fit the gray scale calibration data including preparing a graph and reading the radiance corresponding to each measured film density from this graph. The calibration data are roughly linear through the central portion of the useful film density range if the logarithm of the radiance is plotted as a function of the film density. When the gray scale calibration points and the film densities for the scene fall within this approximately linear range, a least squares regression fit of a third or fourth degree polynomial will produce a satisfactory expression for calculating radiances from measured film densities.

When the film densities cover a wider range, better results can be achieved be devising a more complex mathematical expression which describes the film characteristics, and then using the gray scale calibration data in a regression anaylsis to adjust the constant offset in this expression and its slope in the approximately linear portion of the plot. This procedure has been used to fit the characteristics of the magenta-forming layer of Kodachrome 64 film with a fifth degree polynomial and then to adjust the value of the constant term and the coefficient of the first power of the film density to fit each set of gray scale calibration data. This procedure was used to obtain the data in FIG. 4.

FIG. 4 shows radiance profiles measured close to a scene 12 and farther away from the scene 13. The distance between the cameras was 7.8 km. The abscissa in this figure is the location of the spot on the film whose density was measured. These data have been brought into register by adjusting the scale for curve 13. The position data for curve 13 were adjusted by a linear transformation so that the sharp density changes 14 and 15 occurred at the same scan positions as in curve 12. Other fitting procedures could be used to bring the radiance scans into register.

The radiance curve 12 measured close to the scene gives the initial radiance $I_o$ each point in the scene. The radiance curve 13 gives the apparent radiance I measured at a greater distance. Equation 1 shows that for each point in the scene, these radiances are linearly related, and that the slope of the relationship is the transmittance of the sight path between the camera locations and the intercept is the path radiance. These parameters can be determined by a linear regression analysis. The linear regression analysis was performed for the data in FIG. 4 lying between points 16 and 17. The regression analysis was restricted to this portion of the data so that the sight path from the far camera to the scene passed close to the near camera for all data used in the regression analysis. For these data, it was found that the transmittance of the sight path was 49% and the path radiance was 156 units on the radiance scale used in FIG. 4.

When data from large numbers of photographic images are to be reduced, it is advantageous to automate the data reduction calculations. The data from the densitometer can be read into a computer and then the fitting of the gray scale calibration data, the calculation of radiances for the scans of the scenes, the registration of the scan data, and the calculation of the sight path transmittance and path radiance for a pre-selected portion of the scan carried out automatically. The computer output should include tables of residuals and correlation coefficients, and other parameters characterizing the quality of the fits for purposes of quality control.

Photographic measures of the transmittance of a sight path according to the instant invention have been compared with other measures of transmittance in field experiments. In these experiments, the photographs were taken manually and radios were used to achieve time synchronization. At the same time, transmittance data were obtained by measuring the transmittance of radiance differences with four teleradiometers using the method described by Haecker (1905) (Richards and Stoelting, 1986). Transmittance measurements were also made using a rotating target method described by Richards and Stoelting (1986).

Figure 5:
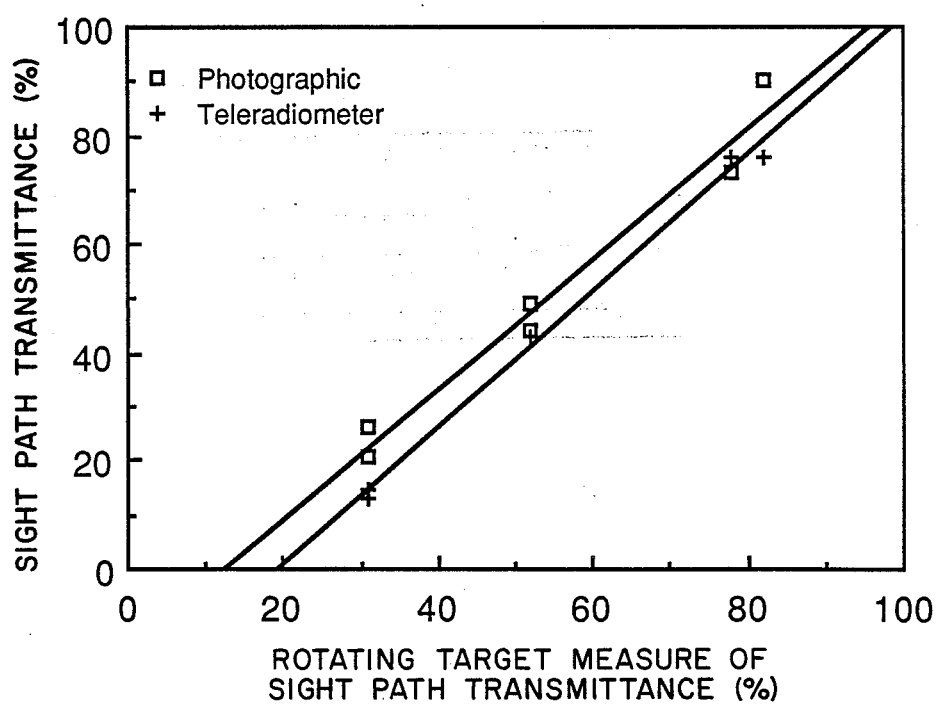
FIG. 5 is a plot comparing sight path transmittance data obtained by the method of the invention with transmittance data obtained by two instrumental measurement methods.

FIG. 5 shows a scatter diagram comparing the data from the three measurements, all of which were under development. More complete development of each method should reduce the scatter in the results. The abscissa in the figure is the transmittance measured by the rotating target method described by Richards and Stoelting (1986). This instrument is a transmissometer which uses a 4 ft diameter diffuse reflector as a light source. The reflector consists of a rotating disk behind a mask with pie-shaped cutouts, and the disk is painted so that the portions which can be seen through the cutouts alternate between all white and all black. The amplitude of the triangular wave light signal is measured close to the rotating target and at a distance of 7.8 km. The transmittance of the sight path is equal to a calibration constant times the signal measured at a distance divided by the signal measured near the rotating target.

The cameras and teleradiometers for the other two measurement methods were set up near the location of the rotating target measurements so that all three measurements were made for the same sight path through the atmosphere. The cameras and teleradiometers were focused on a hillside 4.4 km beyond one end of the sight path. The teleradiometers were used as described by Haecker (1905). Radiance readings for a light-colored grassy area (to the right of 14 in FIG. 4) and a dark-colored tree-covered area (to the left of 14) were taken at each location and the differences in the radiances were calculated. The transmittance of the sight path is the difference in the radiances measured far from the hillside divided by the difference in the radiances measured close to the hillside.

The upper line in FIG. 5 is a least-squares regression line comparing the photographic data to the rotating target transmittance data. The lower line is a least-squares regression line comparing the teleradiometer data to the rotating target transmittance data. The data from the three measurement methods are in general agreement with each other, and the quality of the results is at least comparable to the data obtained by measurement methods now in use (White and Macias 1986). The quality of the agreement between these measurement methods could be improved by refinement of the experimental procedures.

Figure 6:
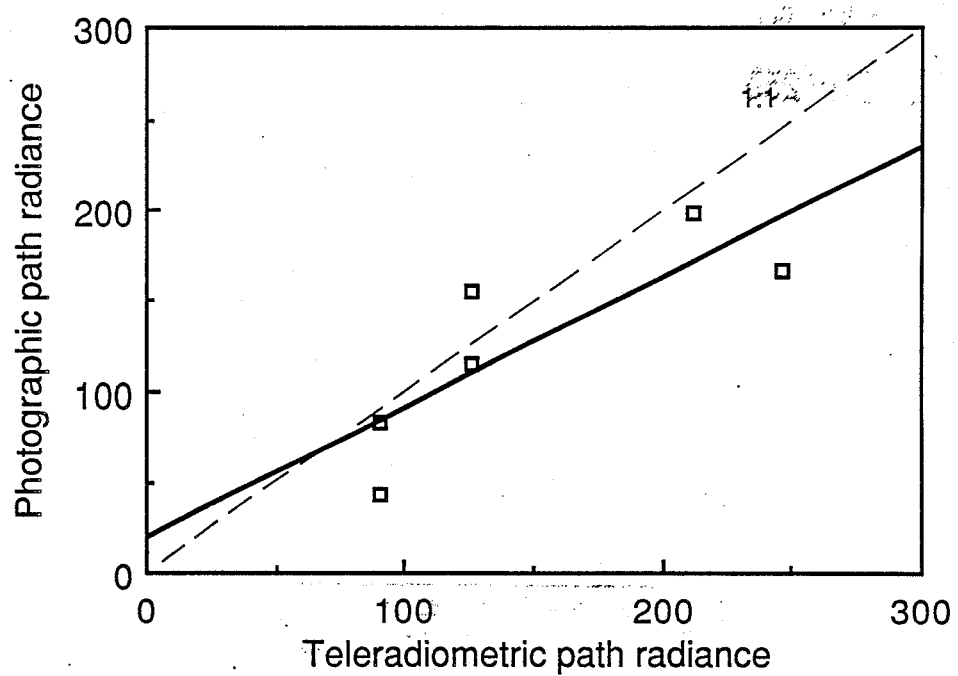
FIG. 6 is a plot comparing path radiance data obtained by the method of the invention with path radiance data obtained by an instrumental method.

The path radiances determined from the photographs are compared with the path radiances calculated from the teleradiometer readings in FIG. 6. The solid line is a least-squares regression line, and the dotted line indicates perfect agreement. Four out of six points show good agreement. It is believed that the film calibration procedures can be improved by using more than six steps in the gray scale and that this would improve the accuracy and precision of the path radiances calculated from the photographs.

While the above invention has been described with reference to particularly preferred embodiments, it will be apparent to those of ordinary skill in the art that modifications may be made to the described apparatus which fall within the scope of the claims appended hereto.

I claim:

1. A method for obtaining quantitative data useful to determine either the transmittance, path radiance, or both, of a sight path toward a target having both relatively light and dark areas using photographic film which comprises the steps of:
   (a) at each of at least two stations along a sight path, providing a camera with photographic film, a calibration scale in the camera's field of view, said scale having panels of known reflectances, a light meter for measuring the radiance of one panel of the calibration scale, and means for synchronizing the time of the photographic exposures;
   (b) at each station along the sight path, photographing a target having varying light contrast substantially synchronously with all other stations;
   (c) at each station along the sight path, at the time the target is photographed per step (b), measuring the radiance of one panel of the calibration scale using the light meter provided in step (a);
   (d) calibrating the film at each station using the light meter measurement of the radiance of one of the calibration panels at each station at the time of the target exposure to calculate the radiances of all panels of the calibration scale and to relate photographic film densities to the radiances of the calibration scale panels; and
   (e) obtaining radiance data for each station along the sight path by using the step (d) radiance calibration obtained by measuring the photographic film densities corresponding to the calibration scale panels and by measuring the film densities for each target photograph for contrasting portions of the target.

2. The method of claim 1 wherein automatic exposure cameras are provided in step (a).

3. The method of claim 1 wherein means for display of the light meter reading within the recorded photographic exposure is further provided in step (a).

4. The method of claim 1 wherein said calibration scales comprise gray scales.

5. The method of claim 1 wherein a preselected colored lens filter is further provided for all cameras and light meters when black and white photographic film is provided in step (a).

6. The method of claim 1 wherein positive color transparency photographic film is provided in step (a).

7. The method of claim 1 wherein means for indicating and displaying the time and date of exposure within the camera field of view or on the recorded photographic exposure is further provided in step (a).

8. The method of claim 1 wherein said target having both relatively light and dark areas is a natural scene.

9. The method of claim 1 wherein said target having both relatively light and dark areas is a scene containing man-made objects.

10. The method of claim 1 wherein said target having both relatively light and dark areas is a target designed specifically for this method.

11. The method of claim 1 wherein the lens focal length of each of said cameras is substantially inversely proportional to the distance between that camera and the target, such that target size on the resulting exposures remains substantially constant along the sight path.

12. A method for determining either the transmittance or path radiance, or both, of a sight path toward a target which comprises the steps of:
  (a) obtaining quantitative film density data for the target photographs containing both the target and calibration scale according to the method of claim 1;
  (b) calculating the radiance of all calibration scale panels in each target photograph by using the known reflectances of the calibration scale panels and the apparent radiance of one calibration scale panel measured by the light meter at the time the specific target photograph was obtained;
  (c) deriving a graph or mathematical expression from this measured and calculated radiance data to relate the radiance of each calibration scale panel to the density of its image recorded on the photographic film;
  (d) converting the measured photographic film density at each point on the scan of the target into the radiance of this point in the target using the graph or mathematical expression derived in step (c); and,
  (e) using equation (1) $I = I_o T + I_p$ wherein I=apparent radiance, $I_o$=initial radiance, T=transmittance and $I_p$=path radiance, for two or more points in the target to calculate either transmittance, path radiance, or both, between camera stations.

13. The method of claim 12 wherein a linear regression analysis for a series of points is used in step (e) to determine values for transmittance, path radiance, or both.

* * * * *